United States Patent [19]

Schneider

[11] Patent Number: 5,836,967

[45] Date of Patent: Nov. 17, 1998

[54] CATHETER ASSEMBLY

[75] Inventor: Ernst Schneider, Langnau am Albis, Switzerland

[73] Assignee: Schneider (Europe) AG, Bulach, Switzerland

[21] Appl. No.: 990,361

[22] Filed: Dec. 15, 1997

[30] Foreign Application Priority Data

Jun. 23, 1997 [EP] European Pat. Off. .............. 97110241

[51] Int. Cl.$^6$ .................................................. A61M 29/00
[52] U.S. Cl. ............................ 606/198; 604/96; 604/101
[58] Field of Search ..................... 604/101, 96; 606/198, 606/192–197; 623/1, 11, 12

[56] References Cited

U.S. PATENT DOCUMENTS

| | | | |
|---|---|---|---|
| 4,573,966 | 3/1986 | Weikl et al. | 604/53 |
| 4,610,662 | 9/1986 | Weikl et al. | 604/53 |
| 4,655,746 | 4/1987 | Daniels et al. | 604/53 |
| 4,994,033 | 2/1991 | Shockey et al. | 604/101 |
| 5,226,889 | 7/1993 | Sheiban | 604/101 |
| 5,279,546 | 1/1994 | Mische et al. | 604/22 |
| 5,320,604 | 6/1994 | Walker et al. | 604/96 |
| 5,397,307 | 3/1995 | Goodin | 604/96 |
| 5,415,636 | 5/1995 | Forman | 604/101 |
| 5,454,788 | 10/1995 | Walker et al. | 604/96 |
| 5,462,529 | 10/1995 | Simpson et al. | 604/101 |
| 5,484,412 | 1/1996 | Prespont | 604/101 |
| 5,514,092 | 5/1996 | Forman et al. | 604/101 |
| 5,569,197 | 10/1996 | Helmus et al. | 604/96 |
| 5,599,329 | 2/1997 | Gabbay | 604/284 |

FOREIGN PATENT DOCUMENTS

| | | |
|---|---|---|
| 0080436 A1 | 11/1982 | European Pat. Off. . |
| 0309469 B1 | 4/1989 | European Pat. Off. . |
| 0604803 A2 | 7/1994 | European Pat. Off. . |
| 95/16487 | 6/1995 | WIPO . |

*Primary Examiner*—Michael Powell Buiz
*Assistant Examiner*—Lien Ngo
*Attorney, Agent, or Firm*—Peter C. Richardson; Lawrence C. Akers; Philip C. Strassburger

[57] ABSTRACT

A catheter assembly for the treatment of vessels carrying body fluid, comprising an inner catheter provided with a guidewire lumen for receiving a guidewire and an inflation lumen for a balloon provided at its distal end. The catheter assembly further comprises an outer catheter provided with an inflation lumen for a balloon provided at its distal end and a lumen in which the inner catheter is applied shiftable for changing the spacing of the two balloons and which features a larger cross-section than that of the inner catheter so that between the outer wall of the inner catheter and the inner wall of the outer catheter a cross-section employable as an inflation lumen exists and ports into the portion sited between the two balloons.

3 Claims, 1 Drawing Sheet

CATHETER ASSEMBLY

BACKGROUND OF THE INVENTION

This application claims priority under 35 U.S.C. § 119 of European Patent Application No. 97110241.3, filed in the European Patent Office on Jun. 23, 1997.

EP 0 080 436 A1 discloses a catheter assembly having an occlusion balloon at both the distal end of the outer catheter and at the distal end of the inner catheter, with the aid of which a vasoconstriction can be isolated. Due to the inner catheter being shift able relative to the outer catheter the spacing of the two balloons can be varied so that the length of the isolated segment of the constriction to be treated can be adapted to the conditions in each case. In this catheter assembly the inner catheter comprises four lumina, one of which has the task of the inflation lumen for the balloon provided on the inner catheter and two further lumina are supply and removal passageways for the therapeutic fluid to be delivered to the constriction site. The fourth lumen arranged centrally in the inner catheter serves with the aid of an overflow passageway as a perfusion lumen which like a bypass duct bypasses the isolated constriction site during treatment and thus maintains the flow of bodily fluid in the vessel also during treatment. Provided between the outer catheter and the inner catheter is an interspace serving as an additional lumen, via which the constriction segment can be treated by supply and removal of an irrigant. The inner catheter of this assembly has a complicated structure and is thus expensive to manufacture. The central lumen cannot be occluded distally and can thus not serve as an infusion lumen.

A further catheter assembly of the aforementioned kind is known from U.S. Pat. No. 4,655,746. In this known catheter assembly the inner catheter has only one lumen simultaneously serving as guidewire lumen and inflation lumen for the occlusion balloon provided at the distal catheter end. The guidewire lumen must thus be permanently occluded at the distal catheter end so that it can be put to use simultaneously as an inflation lumen. For delivering the therapeutic fluid to the segment isolated by the two balloons only the interspace between the outer catheter and the inner catheter is available. Optionally it is also possible to provide in the inner catheter a supply passageway for the therapeutic fluid which, however, results in a complicated configuration of the inner catheter as well as involving an increase in the overall profile of the catheter assembly.

In a catheter assembly known from EP 0 309 469 B1 two occlusion balloons for isolating the constriction to be treated are provided, delivery of the therapeutic agent being possible exclusively via the interspace between the inner catheter and the outer catheter. Simultaneously infusing a therapeutic fluid and drawing it off from the segment being treated is not possible with this catheter assembly.

In the catheter assembly likewise provided with two occlusion balloons as disclosed by U.S. Pat. No. 5,279,546 a total of six lumina exist in the outer catheter, four of which can serve as infusion lumens, the guidewire lumen too, in the inner catheter, configured with three lumina permitting employment as infusion lumens. In the complicated structure of this catheter assembly no interspace is provided between the outer catheter and the inner catheter and thus friction forces occur, making it difficult to shift the inner catheter relative to the outer catheter. Additional partitions and lumina for the electrical power leads of an ultrasonic transmitter enlargen the overall cross-section of this catheter assembly. The ultrasonic transmitter restricts adjustability of the balloon spacing and can obstruct delivery of the therapeutic agent into the balloon interspace.

All documents cited herein, including the foregoing, are incorporated herein by reference in their entireties for all purposes.

SUMMARY OF THE INVENTION

The invention is based on the object of defining a catheter assembly of the aforementioned kind in which the inner and outer catheter are easily shiftable relative to each other and the balloon spacing is adjustable over a large segment length. In addition, it is intended that the catheter assembly features a simple configuration providing lumina having large bores for supply and removal of the therapeutic agent in a low overall profile.

In the catheter assembly in accordance with the invention the guidewire lumen of the inner catheter can be made use of additionally to its function as the guidewire lumen also as the infusion lumen for supply and removal of a therapeutic fluid since the ports in the catheter wall in the portion between the two balloons produce a flow connection to the vessel segment to be treated. By suitably selecting the cross-section of the guidewire lumen the suitability of this lumen as an infusion lumen is further enhanced. So that the guidewire lumen can actually also be employed as an infusion lumen an occlusion element is fitted to its distal end which can occlude the port of the guidewire lumen so that the therapeutic fluid cannot emerge from this port, it instead gaining access through these ports to the portion between the two balloons.

Configuring one of the balloons as a dilatation balloon opens up new fields of application for the catheter assembly when a constriction is present in the vessel segment to be treated. For this purpose the balloon configured as a dilatation balloon is employed in a pretreatment stage to physically dilate the constriction. As appreciated by the person skilled in the art the balloon in its function as a dilatation balloon needs to satisfy criteria other than those of a pure occlusion balloon which simply has the function of occluding a vessel carrying body fluid. In this arrangement the special requirements made on the dilatation balloon relate to both its geometry and material selection.

In sum, the present invention relates to a catheter assembly for the treatment of vessels carrying body fluid. An inner catheter is provided with a guidewire lumen for receiving a guidewire and an inflation lumen for a balloon provided at its distal end. An outer catheter is provided with an inflation lumen for a balloon provided at its distal end and a lumen in which the inner catheter is applied shiftable for changing the spacing of the two balloons and which features a larger cross-section than that of the inner catheter so that between the outer wall of the inner catheter and the inner wall of the outer catheter a cross-section employable as an inflation lumen exists and ports into the portion sited between the two balloons. The guidewire lumen of the inner catheter is connected to the portion sited between the two balloons via ports in the catheter wall, the guidewire lumen is dimensioned cross-sectionally so that it can be used as the inflation lumen also when the guidewire is in the lying position, the guidewire is provided at its distal end with an occlusion element for closing off the port located at the distal end of the guidewire lumen. One of the two balloons may be configured as a dilatation balloon, such as the balloon attached to the distal end of the inner catheter.

BRIEF DESCRIPTION OF THE DRAWINGS

An example embodiment of the invention will now be explained with reference to the drawings in which.

DETAILED DESCRIPTION OF THE INVENTION

Figure 1:
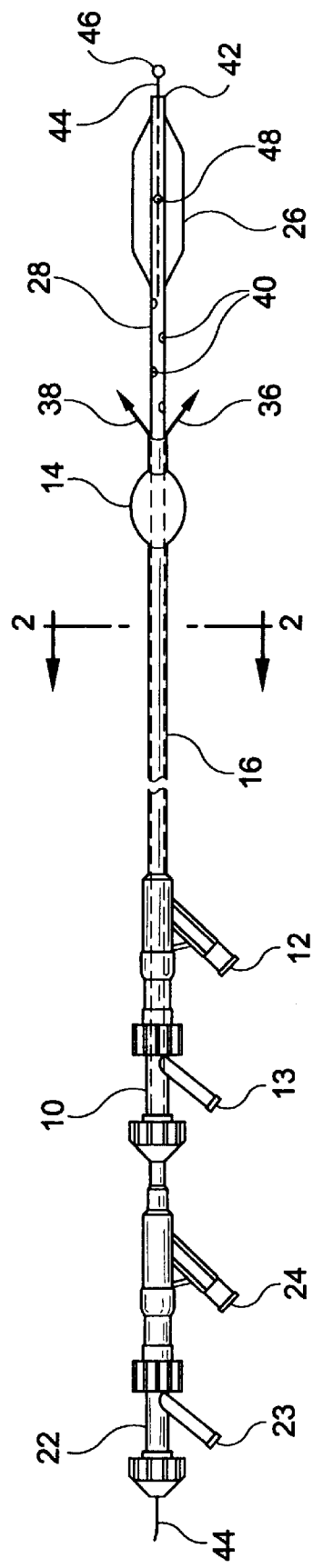
FIG. 1 is a schematic overall view of the catheter assembly in accordance with the invention and FIG. 2 is a sectional view taken along the line 2—2 in FIG. 1.
Figure 2:
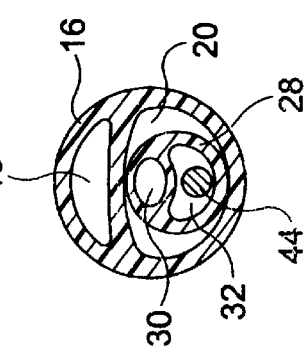

The catheter assembly as shown in FIG. 1 consists of an outer catheter having a Y-connector 10, an inflation connection 12 for supplying a pressurizing medium to an occlusion balloon attached to the distal end of this outer catheter, as well as a catheter stem 16. As evident from the sectional view as shown in FIG. 2 the stem 16 of the outer catheter is configured with two lumina, the lumen 18 serving to supply the pressurizing medium to the occlusion balloon 14 whilst via the lumen 20 a therapeutic agent, for example a thrombolytic agent, can be delivered to the vessel segment to be treated.

The catheter assembly contains furthermore an inner catheter having a Y-connector 22, an inflation connection 24 for supplying a pressurizing medium to a dilatation balloon 26 attached to the distal end of this inner catheter, as well as a catheter stem 28. As evident from the sectional view as shown in FIG. 2 the stem 28 of the inner catheter is configured with two lumina, the lumen 30 serving to supply the pressurizing medium to the dilatation balloon 26 whilst the lumen 32 serves to receive a guidewire 44.

The outer catheter lumen 20 receiving the inner catheter features a substantially larger cross-section than that of the stem 28 of the inner catheter so that even after the inner catheter has been introduced into the lumen 20 a larger flow cross-section is available for the delivery of the therapeutic fluid. Also the inner catheter lumen 32 receiving the guidewire 44 has a cross-section substantially larger than that of the guidewire cross-section so that this lumen too, can be used as a flow path for the therapeutic fluid. This also ensures facilitated sliding action of inner and outer catheter.

The arrows 36, 38 in FIG. 1 indicate how the therapeutic fluid supplied via a connection 13 on the Y-connector 10 gains access to the portion between the two balloons from the interlumen. So that the guidewire lumen can be put to use in delivering the therapeutic fluid, ports 40 are provided in the portion between the two balloons 14, 26 in the stem of the inner catheter, the therapeutic fluid being able to flow through these ports. To prevent the therapeutic fluid, delivered via a connection 23 on the Y-connector 22 and flowing through the guidewire lumen 32, from emerging from the port 42 at the distal end of the inner catheter, the guidewire 44 is provided at its end with an occlusion element 46 which is able to come into contact with the port 42 by the guidewire being retracted so that the port is occluded.

The catheter assembly described can be put to use as follows in the treatment of a constriction. Firstly, the catheter assembly is advanced to such an extent in the vessel carrying the body fluid that the dilatation balloon 26 is precisely located at the constriction site, the location of the dilatation balloon 26 being able to be monitored on the x-ray monitor as usual with the aid of a metal marker 48 attached to the stem 28 within the dilatation balloon 26. By supplying a pressurizing medium via the connection 24 the dilatation balloon 26 can be expanded, resulting in dilatation of the constriction to be treated. Once this dilatation action has been implemented the pressurizing medium is first drained from the dilatation balloon 26 and the inner catheter is advanced into the vessel beyond the constriction to be treated until it is downstream thereof, the occlusion balloon 14 remaining thereby in the portion upstream of the constriction. A pressurizing medium is then supplied to the two balloons via the connections 24 and 12 so that both balloons are distended to isolate the vasoconstriction. The therapeutic fluid acting as desired on the calcarious and fatty tissue forming the constriction can now be delivered via the connection 23 of the Y-connector 22 into the isolated portion between the two balloons 14 and 26. Drawing off this fluid can then be done via the ports 40 in the stem 28 of the inner catheter and via the guidewire lumen, it, of course, also being possible to deliver the therapeutic fluid via the guidewire lumen 32 of the inner catheter and to drain it off via the lumen 20 in the outer catheter.

Throughout the complete duration of treatment the guidewire 44 must, of course, be retracted in the guidewire lumen 32 sufficiently so that the occlusion element 46 is in contact with the port 42 at the distal end of the inner catheter and occludes this port 42, it only being then that the guidewire lumen 32 can be employed as the lumen for supply and removal of the therapeutic fluid.

On termination of the residence time in which the therapeutic fluid is allowed to react on the tissue of the constriction and after the therapeutic fluid has been drawn off from the isolated constriction segment the pressurizing medium is drained from the two balloons 14 and 26 so that the catheter assembly can be removed from the vessel.

Due to its configuration as described the present catheter assembly provides a large flow cross-section for the therapeutic fluid whilst nevertheless having a low profile overall facilitating its placement even in narrow vessels having constrictions to be treated. The balloon spacing and thus the length of the vessel segment to be treated are variable over a broad range.

The above-described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A catheter assembly for the treatment of vessels carrying body fluid, comprising:

an inner catheter provided with a guidewire lumen for receiving a guidewire and an inflation lumen for a balloon provided at its distal end, an outer catheter provided with an inflation lumen for a balloon provided at its distal end and a lumen in which the inner catheter is applied shiftable for changing the spacing of said two balloons and which features a larger cross-section than that of said inner catheter so that between the outer wall of said inner catheter and the inner wall of said outer catheter a cross-section employable as an inflation lumen exists and ports into the portion sited between said two balloons, wherein said guidewire lumen of said inner catheter is connected to said portion sited between said two balloons via ports in said catheter wall, said guidewire lumen is dimensioned cross-sectionally so that it can be used as said inflation lumen also when said guidewire is in the lying position, said guidewire is provided at its distal end with an occlusion element for closing off said port located at the distal end of said guidewire lumen.

2. The catheter assembly of claim 1 wherein one of said two balloons is configured as a dilatation balloon.

3. The catheter assembly of claim 1 wherein said balloon attached to the distal end of said inner catheter is configured as a dilatation balloon.

* * * * *